United States Patent
Xanthis et al.

(10) Patent No.: US 12,260,951 B2
(45) Date of Patent: Mar. 25, 2025

(54) METHOD FOR SIMULATION OF A MAGNETIC RESONANCE SCANNER

(71) Applicant: CORSMED AB, Stockholm (SE)

(72) Inventors: Christos Xanthis, Athens (GR); Anthony Aletras, Salonika (GR)

(73) Assignee: CORSMED AB, Stockholm (SE)

( * ) Notice: Subject to any disclaimer, the term of this patent is extended or adjusted under 35 U.S.C. 154(b) by 93 days.

(21) Appl. No.: 18/008,281

(22) PCT Filed: Jun. 9, 2021

(86) PCT No.: PCT/SE2021/050550
§ 371 (c)(1),
(2) Date: Dec. 5, 2022

(87) PCT Pub. No.: WO2021/251884
PCT Pub. Date: Dec. 16, 2021

(65) Prior Publication Data
US 2023/0245759 A1    Aug. 3, 2023

(30) Foreign Application Priority Data

Jun. 10, 2020   (SE) .................................. 2050683-8

(51) Int. Cl.
*A61B 5/055*     (2006.01)
*G16H 30/20*     (2018.01)

(52) U.S. Cl.
CPC ............. *G16H 30/20* (2018.01); *A61B 5/055* (2013.01)

(58) Field of Classification Search
CPC ........ G16H 30/20; G16H 50/50; A61B 5/055; G01R 33/5608; G09B 23/286
See application file for complete search history.

(56) References Cited

U.S. PATENT DOCUMENTS

| 2016/0259023 A1 | 9/2016 | Overall et al. |
| 2019/0154783 A1 | 5/2019 | Kaditz et al. |
| 2019/0365335 A1 | 12/2019 | Hunt et al. |

FOREIGN PATENT DOCUMENTS

| EP | 3415939 A1 | 12/2018 |
| EP | 3531159 A1 | 8/2019 |

(Continued)

OTHER PUBLICATIONS

Machine translation of foreign patent application publication JP-2017-140165-A (Year: 2017).*

(Continued)

*Primary Examiner* — G. M. A Hyder
(74) *Attorney, Agent, or Firm* — MOSER TABOADA

(57) ABSTRACT

The present invention describes a method for simulation of a magnetic resonance (MR) scanner in an MRI simulator, said method comprising—input of data parameters into a web interface of the MRI simulator, wherein the input of data parameters is at least a pulse sequence and an anatomical model;—connection of the web interface with a cloud-based simulator engine of the MRI simulator for transfer of data parameters to the cloud-based simulator engine, said method involving—importing a pulse sequence calculation model;—setting input data; and—performing a slice selection in an obtained image in the web interface; said method also involving—recalculation of the data parameters for the provision of one or more simulated MR signals, said recalculation being performed in the loud, and wherein the method also comprises—reconstruction of an MR image based on said one or more simulated MR signals, said econstruction of an MR image being performed in the cloud; and—sending the MR image to the web interface.

6 Claims, 2 Drawing Sheets

(56) References Cited

FOREIGN PATENT DOCUMENTS

| JP | 2017140165 A | * | 8/2017 | ............. A61B 5/055 |
|----|--------------|---|--------|--------------------------|
| WO | WO-2017/079178 A1 | | 5/2017 | |
| WO | WO-2017/090044 A1 | | 6/2017 | |
| WO | WO-2018/106713 A1 | | 6/2018 | |
| WO | WO-2020/036861 A1 | | 2/2020 | |

OTHER PUBLICATIONS

Xanthis, et al.; coreMRI: A high-performance, publicly available MR simulation platform on the cloud; Plos One; https://doi.org/10.1371/journal.pone.0216594; May 17, 2019; pp. 1-26.

Xanthis, et al.; Simulator-generated training datasets as an alternative to using patient data for machine learning: An example in myocardial segmentation with MRI; Computer Methos and Programs in Biomedicine; www.elsevier.com/locate/cmpb; [m5G; Nov. 4, 2020; 20:33].

International Search Report & Written Opinion mailed Aug. 26, 2021 for Application No. PCT/SE2021/050550, 10 pages.

Xanthis, et al., "coreMRI: A high-performance, publicly available MR simulation platform on the cloud", Plos One / https://doi.org/10.1371/journal.pone.0216594; May 17, 2019, 26 pages.

* cited by examiner

METHOD FOR SIMULATION OF A MAGNETIC RESONANCE SCANNER

FIELD OF THE INVENTION

The present invention relates to a method for simulation of a magnetic resonance scanner.

SUMMARY OF THE INVENTION

The present invention is directed to a method for simulation of a magnetic resonance (MR) scanner in an MRI simulator, said method comprising
  input of data parameters into a web interface of the MRI simulator, wherein the input of data parameters is at least a pulse sequence and an anatomical model;
  connection of the web interface with a cloud-based simulator engine of the MRI simulator for transfer of data parameters to the cloud-based simulator engine, said method involving
  importing a pulse sequence calculation model;
  setting input data; and
  performing a slice selection in an obtained image in the web interface; said method also involving
  recalculation of the data parameters for the provision of one or more simulated MR signals, said recalculation being performed in the cloud, and wherein the method also comprises
  reconstruction of an MR image based on said one or more simulated MR signals, said reconstruction of an MR image being performed in the cloud; and
  sending the MR image to the web interface.

In "coreMRI: A high-performance, publicly available MR simulation platform on the cloud", PLOSONE, Christos G. Xanthis, Anthony H. Aletras, there is disclosed a cloud-oriented engine for advanced MRI simulations (coreMRI). The aim of the study was to develop the first advanced MR simulation platform delivered as a web service through an on-demand, scalable cloud-based and GPU-based infrastructure. As mentioned, the online MR simulation platform could be utilized as a virtual MRI scanner but also as a cloud-based, high-performance engine for advanced MR simulations in simulation-based quantitative MR (qMR) methods. In the method used, there is also performed slicing to enable the MRI simulation procedure. It should be noted that the approach suggested according to the present invention is not disclosed or hinted in this article.

The present invention provides an improved method for the implementation of a cloud-based MR simulation, such as for the procedures provided in the article mentioned above. The improvements provided by the present invention relate to the slice procedures and e.g. also on the system level referring to how different units interact which other (CPUs, GPUs, user interface etc.).

Specific Embodiments of the Invention

Some specific embodiments according to the present invention are provided below and further described.

According to the present invention, the method also involves reconstruction of an MR image based on said one or more simulated MR signals, said reconstruction of an MR image being performed in the cloud; and sending the MR image to the web interface.

As should be understood from above, the reconstruction is a step that follows the actual simulation according to the present invention. Reconstruction may be part of the method according to the present invention, but it should also be said that the method according to the present invention also embodies cases when raw data is the directed intended output or cases of simulation-based quantitative MR.

According to yet another specific embodiment of the present invention, the input of data parameters is at least a pulse sequence and an anatomical model. Also, other parameters may be input in the method according to the present invention. For instance, general configurations may be specified as such input.

Furthermore, and as may be understood from above, the method according to the present invention also has a clear direction towards the interaction of different interfaces and units involved in a platform system according to the present invention. In this context it may be mentioned that the present invention has a clear direction towards providing a platform for analytical or numerical MRI simulations for educational purposes wherein the platform is GPU (graphics processing unit)-based, cloud-based and also web-based. There are also other applications of interest according to the present invention, such as for research and AI purposes.

Moreover, in this regard it may also be said that according to one specific embodiment, the cloud-based simulator engine performs the recalculation and sends recalculated data to one or more GPUs (graphics processing units) of the MRI simulator, which GPUs sends back said one or more simulated MR signals.

Furthermore, according to yet another specific embodiment of the present invention, the step of reconstruction of an MR image is performed by one or more CPUs (central processing units) and/or one or more GPUs (graphics processing units) of the MRI simulator in the cloud.

In this context it may also be mentioned that the characteristics/specs of the GPU cards define how the experiment will break down in smaller pieces. Moreover, there may be GPU-resource limits (such as maximum threads, shared memory capacity, maximum registers per thread, register file capacity, etc) that may cap GPU utilization. An optimal GPU card would allow the transfer, host and execution of the entire experiment in one iteration without breaking the experiment down in smaller pieces and without decreasing GPU utilization. Such an optimal GPU card would achieve maximum GPU utilization when the cumulative demands of the resources equal the GPU's resource capacity with respect to the kernel's requirements. According to the present invention different types of calculation tools and software may be used, also for the coding of parts of the method being performed. According to one specific embodiment, MATLAB is used for performing at least parts of the recalculation.

As mentioned above, different form of input is provided to a system according to the present invention, i.e. so that the method may be performed. One such parameter is the pulse sequence used. In line with this, and to set a definition, according to one specific embodiment, a pulse sequence is a sequence of events which change how every point in space should behave to generate a signal. Again, also general configurations may be set input according to the present invention. Examples are the type of coordinate system used and if it is e.g. based on a 3D or a 4D model. Furthermore, also the actual anatomical model used is one such parameter defining the starting point for the system and as such the method according to the present invention. In this regard it may also be mentioned that the anatomical model may be human or animal. Also, phantom objects, and in fact any other type of object, are totally possible. It should, however, be mentioned that human or animal anatomical models are a key focus for the method and system according to the present invention.

According to the present invention, the procedure of the steps of input of data parameters into a web interface of the MRI simulator; and connection of the web interface with a cloud-based simulator engine of the MRI simulator for transfer of data parameters to the cloud-based simulator engine;

preferably involves importing a pulse sequence calculation model;

setting input data; and performing a slice selection in an obtained image in the web interface.

In this regard it should be mentioned that the pulse sequence calculation model may involve several parameters, which at least some of them are possible to adjust. One such adjustable example is contrast. Also the slicing as such is a relevant aspect according to the present invention. According to one specific embodiment of the present invention, each new slice selection functions as a reference for a next slice selection. Moreover, according to yet another embodiment, phase encoding direction and frequency encoding direction represent one axis each orthogonal to the slice selection direction. For instance, in a given X, Y and Z coordinate, these two parameters may be represented in X and Y, respectively.

Moreover, according to one embodiment, the slice selection is a single slice selection 2D acquisition(s) or a slab in 3D acquisition(s).

Furthermore, and as a continuation of the above, according to yet another specific embodiment of the present invention, the following procedure is performed:

performing a slice selection in an obtained image in the web interface;

a new image is obtained;

a new slice selection is performed in a different direction;

a new image is obtained; and finally yet another slice selection is performed, and wherein each image obtained preferably is a cross sectional plane to the image in which the slice selection is performed.

The change of direction when slicing possible to use in the method according to the present invention enables to obtain a further improved image in some cases.

In general, the method according to the present invention finds great use for education purposes in the field of MR imaging. As an example, planning of slicing may be trained in a very efficient way when using the method according to the present invention. Furthermore, the method also enables for a user to understand the physics behind the anatomical model from a MR imaging perspective. It may, however, again be said that the present invention also finds use in several other application, e.g. within research, AI etc.

Furthermore, as the method according to the present invention enables to use, i.e. import, different pulse sequences, calculation models and also different types of slicing protocols, the method may be used on more or less any type of anatomical model, human or animal.

Figure 1:
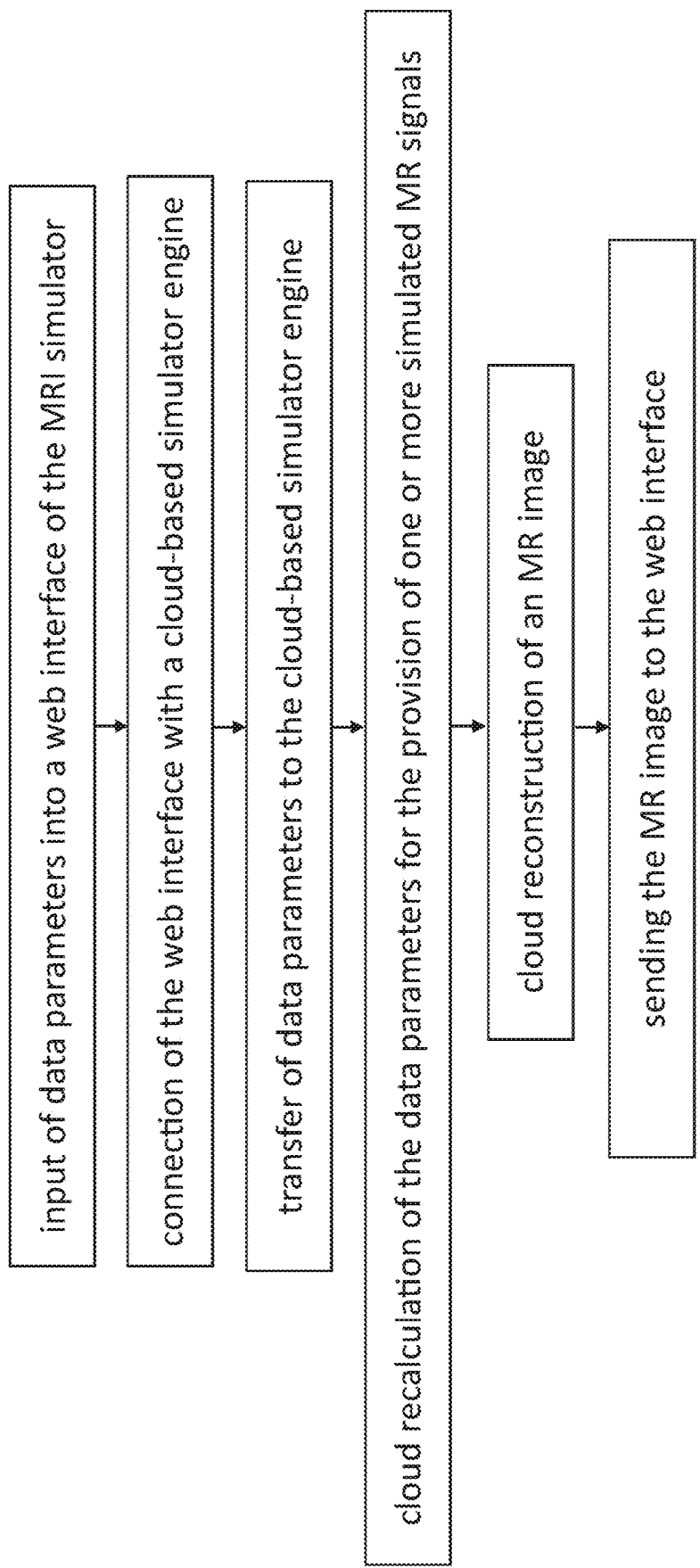
In FIG. 1 there is shown a process scheme of one embodiment of the method according to the present invention.
Figure 2:
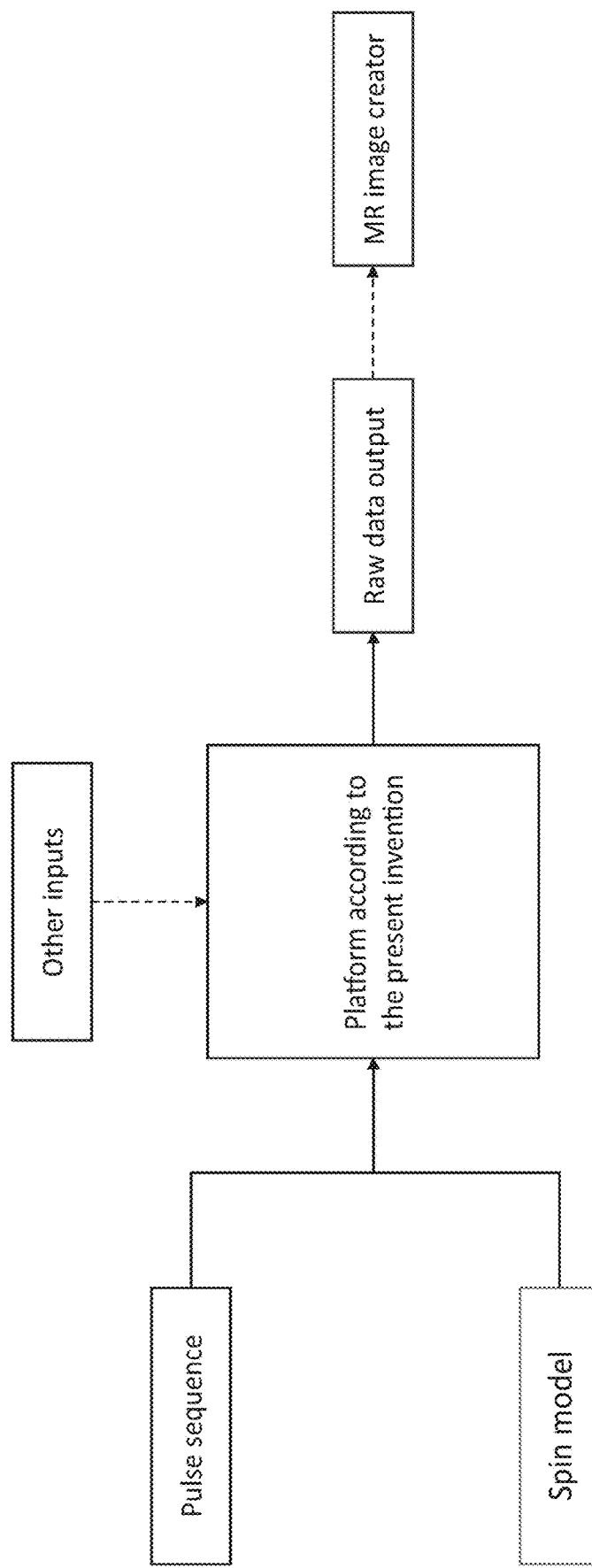
In FIG. 2 there is shown a block scheme of a system setup for interaction with a platform and method according to the present invention.

The invention claimed is:

1. A method for simulation of a magnetic resonance (MR) scanner in an MRI simulator, said method comprising:

inputting data parameters into a web interface of the MRI simulator, wherein the inputting is at least data parameters relating to a pulse sequence and an anatomical model;

connecting the web interface with a cloud-based simulator engine of the MRI simulator for transfer of data parameters to the cloud-based simulator engine;

importing a pulse sequence calculation model, thereby building a pulse sequence during the simulation;

setting input data;

performing a slice selection in an obtained image in the web interface;

recalculating the data parameters for the provision of one or more simulated MR signals, said recalculating being performed in the cloud reconstructing an MR image based on said one or more simulated MR signals, said reconstructing being performed in the cloud; and sending the MR image to the web interface, wherein phase encoding direction and frequency encoding direction represent one axis each orthogonal to the slice selection direction, and wherein the slice selection is a single slice selection 2D acquisition(s) or a slab in 3D acquisition(s).

2. The method according to claim 1, wherein the cloud-based simulator engine performs the recalculating and sends recalculated data to one or more GPUs (graphics processing units) of the MRI simulator, which GPUs sends back said one or more simulated MR signals.

3. The method according to claim 1, wherein the reconstructing is performed by one or more CPUs (central processing units) and/or one or more GPUs (graphics processing units) of the MRI simulator in the cloud.

4. The method according to claim 1, wherein a pulse sequence is a sequence of events which change how every point in space should behave to generate a signal.

5. The method according to claim 1, wherein each new slice selection functions as a reference for a next slice selection.

6. The method according to claim 1, comprising:

performing a slice selection in an obtained image in the web interface;

obtaining a new image;

performing a new slice selection in a different direction;

obtaining another new image; and finally performing yet another slice selection wherein each image obtained preferably is a cross sectional plane to the image in which the slice selection is performed.

* * * * *